(12) United States Patent
Berry

(10) Patent No.: US 6,391,047 B1
(45) Date of Patent: May 21, 2002

(54) REPAIR OF RUPTURED MEMBRANE BY INJECTION OF NATURALLY OCCURRING PROTEIN IN AMNIOTIC FLUID SAC

(76) Inventor: David Berry, 3916 Avenue H, Austin, TX (US) 78751

( * ) Notice: Subject to any disclaimer, the term of this patent is extended or adjusted under 35 U.S.C. 154(b) by 0 days.

(21) Appl. No.: 09/551,415

(22) Filed: Apr. 18, 2000

(51) Int. Cl.[7] .......................... A61B 17/08; C07K 14/00; A01N 37/02
(52) U.S. Cl. ....................... 606/213; 128/898; 530/367; 530/387.3; 514/546; 435/69.1; 435/325
(58) Field of Search .................. 606/213, 10; 128/898; 514/546, 549, 552, 560; 530/367, 387.3, 388.5; 435/69.1, 69.8, 71.1, 69.7, 325

(56) References Cited

U.S. PATENT DOCUMENTS

| | | | | |
|---|---|---|---|---|
| 3,982,040 A | * | 9/1976 | Oborn | 426/614 |
| 5,190,916 A | * | 3/1993 | Adachi | 514/8 |
| 6,060,636 A | * | 5/2000 | Yahiaoui et al. | 604/367 |
| 6,168,849 B1 | * | 1/2001 | Braverman et al. | 428/137 |

OTHER PUBLICATIONS

Awade et al., "Two–step chromatographic procedure for the purification of hen egg white ovomucin, lysozyme, ovotransferrin and ovalbumin and characterization of purified proteins," *J. Chromat. A*, 677:279–288, 1994.

Awade and Efstathiou, "Comparison of three liquid chromatographic methods for egg–white protein analysis," *J. Chromat. B*, 723:69–74, 1999.

Bejar et al., "Premature labor. II. Bacterial sources of phospholipase," *Obstet. Gynecol.* 57:479–482, 1981.

Galask et al., "Bacterial attachment to the chorioamniotic membranes," *Am. J. Obstet. Gynecol.* 148:915–928, 1984.

Huddleston, "Preterm labor," *Clin. Obstet. Gynecol.* 25:123–136, 1982.

Imanaka and Ogita, "New technologies for the management of preterm premature reupture of membranes," *Obstetrics & Gynecology Clinics of N. Am.*, 19:366–386, 1992.

Luks et al., "Gelatin sponge plug to seal fetoscopy port sites: technique in ovine and primate models"; *Am J. Obstet Gynecol*, 181:995–996, 1999.

MacDonnell et al., "The functional properties of the egg–white proteins," *Food Technol.* 9:49–53, 1955.

Miller et al., "Bacterial colonization of amniotic fluid from intact fetal membranes," *Am. J. Obstet. Gynecol.* 136:796–804, 1980.

Rabouille et al., "Interactions involved in ovomucin gel–forming properties: a rheological–biochemical approach," *Archives of Biochem & Biophys.*, 270:495–503, 1989.

Rabouille et al., "The Supramolecular Organization of Ovomucin. Biophysical and Morphological Studies," *Biochemical Journal*, 266:697–706, 1990.

Saade et al., "Amniotic septostomy for the treatment of twin oligohydramnios–polyhydramnios sequence," *Fetal Diagn Ther*, 13:86–93, 1998.

Strecker et al., "$^1$H and $^{13}$C–NMR assignments for sialylated oigosaccharide–alditols related to mucins. Study of thirteen components from hen ovomucin and swallow nest mucin," *Biochimie* 74:39–52, 1992.

* cited by examiner

Primary Examiner—Gary Jackson
(74) Attorney, Agent, or Firm—Fulbright & Jaworski

(57) ABSTRACT

The present invention provides compositions and methods for use in treatment of premature rupture of membrane. The compositions of the invention include a therapeutic amount of an avian thick egg white composition. Preferably, the compositions include the purified thick egg white protein, ovomucin. The methods of the invention involve injecting an effective amount of the compositions into the prematurely ruptured amniotic sac of a patient in order to seal the rupture.

22 Claims, 4 Drawing Sheets

REPAIR OF RUPTURED MEMBRANE BY INJECTION OF NATURALLY OCCURRING PROTEIN IN AMNIOTIC FLUID SAC

BACKGROUND OF THE INVENTION

1. Field of the Invention

The present invention relates generally to the fields of obstetrics and/or perinatal medicine. More particularly the invention relates to repair of pre-parturition rupture of the amniotic fluid sac.

2. Description of Related Art

Premature rupture of membranes (PROM) during the second and early third trimester of human pregnancy creates a management dilemma for obstetricians. There are currently many management protocols for PROM. Recent literature argues the risks and benefits of tocolytic agents, antibiotics, and corticosteroid injections primarily for delaying delivery, preventing intraamniotic infection, and enhancing fetal maturity, respectively, in the event of almost certain preterm delivery. However, to date, no true accepted treatment for PROM exists. Medline searches of this topic reveal only scant data in Italian studies on intracervical instillation of fibrin glue, and Japanese attempts at mechanical blockage of the cervix using double balloon-tipped catheters.

The ideal therapy for PROM in the absence of chorioamnionitis, and deciduitis (infections implicated in premature rupture and preterm labor) would seem to be to recreate an intact amniotic fluid sac using a benign sealant injected into the amniotic sac using needles no bigger than those now commonly used for amniocentesis. By recreating the integrity of the amnion, such a technique would provide a barrier to ascending infection from the normal bacterial flora of the cervix and vagina commonly isolated in most all obstetric and gynecologic infections. Such a technique would also allow reaccumulation of normal amniotic fluid volumes, thus protecting the fetus from compression of its own umbilical cord.

Chicken egg white is a cross species analog to amniotic fluid, providing protection, cushioning, and nutritive substances essential to the survival of the unborn chick. The cross linking of this colloid substance at the site of membrane rupture in the human gestation may provide an adequate sealant in the event of PROM. The inherent properties of egg white colloid include immiscibility with water (hydrophobic), thus creating a bolus effect when encountering the leakage site after injection into a water filled cavity. The most gelatinous portion of the thick egg white component is of substantially low enough viscosity to allow injection via a standard 18 to 20 gauge spinal needle commonly used for amniocentesis.

SUMMARY OF THE INVENTION

The present invention overcomes these and other drawbacks of the prior art by providing methods and compositions for treating premature rupture of membranes (PROM) during pregnancy. The methods and compositions provided result in prolonged gestation, decreased risk of infection and umbilical cord compression, and an increased likelihood of a mature fetus.

In one aspect, the invention provides a method of sealing a ruptured amniotic membrane by introducing an effective amount of an avian thick egg white composition into an amniotic fluid sac of a mammal. It is envisioned that the thick egg white from any type of avian egg will be effective in the present invention. The preferred composition will include chicken thick egg white. For administration of the into the amniotic fluid sac of a mammal, it is preferred that the composition additionally include any known pharmaceutically acceptable carrier. It is not believed that the pharmaceutically acceptable carrier is absolutely necessary in the method of the invention, however.

It is believed that the component of thick egg white that is most important in accomplishing the objectives of the invention is the protein known as ovomucin. Therefore, in preferred embodiments, the composition for use in the method of the invention includes isolated and purified ovomucin or an ovomucin composition. It is envisioned that the ovomucin in the composition of the invention may be present in concentrations of about 1 to 90 percent by weight. It will be understood that this range of concentrations includes all integers and fractions contained between the range of 1 to 90 percent. That is, the range is meant to include concentrations of 1, 2, 3, 4 . . . 10, 11, 12, 13, 14, . . . 20, 21, 22, 23, 24, . . . 30, 31, 32, 33, 34, . . . 50, 51, 52, 53, 54, . . . 80, 81, 82, 83, 84, . . . and so on, including fractions of a percentage, such as 1.1, 1.2, 1.3, . . . 2.1, 2.2, 2.3, . . . 5.1, 5.2, 5.3, . . . 10.1, 10.2, 10.3. . . and so on up to about 90 percent by weight.

In certain preferred embodiments, the thick egg white composition further comprises one or more antibiotics.

The thick egg white composition for use in the method of the invention will typically be introduced into the amniotic sac by an injection procedure, such as an amnioinfusion procedure.

Another aspect of the invention provides a method of enhancing the integrity of a ruptured amniotic membrane by contacting the ruptured amniotic membrane with an effective amount of an avian egg white glycoprotein composition. Preferably, the avian egg white composition will be a chicken thick egg white composition. Most preferably, the thick egg white composition will include a pharmaceutically acceptable carrier. The thick egg white composition will generally comprise an ovomucin composition where the ovomucin will be isolated substantially away from other thick egg white components and purified. The ovomucin may be present in concentrations of 1 to about 90 percent by weight. In certain preferred embodiments, the thick egg white composition will further include one or more antibiotics.

It is envisioned that the thick egg white composition will typically be introduced into the amniotic sac of a patient using an injection procedure. Preferably, the injection procedure will be an amnioinfusion procedure, such as amniocentesis.

Another embodiment of the present invention provides a pharmaceutical amniotic membrane sealant composition comprising an effective amount of a sterile avian egg white glycoprotein composition and one or more pharmaceutically acceptable preservatives. The composition of the invention may further include a pharmaceutically acceptable carrier and/or at least one antimicrobial agent in a therapeutically effective amount.

The present invention further provides a kit for use in a method of sealing a ruptured amniotic membrane including a thick egg white glycoprotein composition in a suitable vial or container. Preferably, the thick egg white composition will include isolated and purified ovomucin with a purity of about 80% to about 95%. The egg white composition may be present in the vial in powder form or gel form or in a solution including a pharmaceutically acceptable preservative and/or a pharmaceutically acceptable carrier. In certain aspects, such as when the composition is in powder or gel form, a pharmaceutically acceptable carrier may be added directly to the vial, mixed gently, drawn into an appropriate needle for injection, and injected into a patient having a ruptured amniotic membrane.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1A:
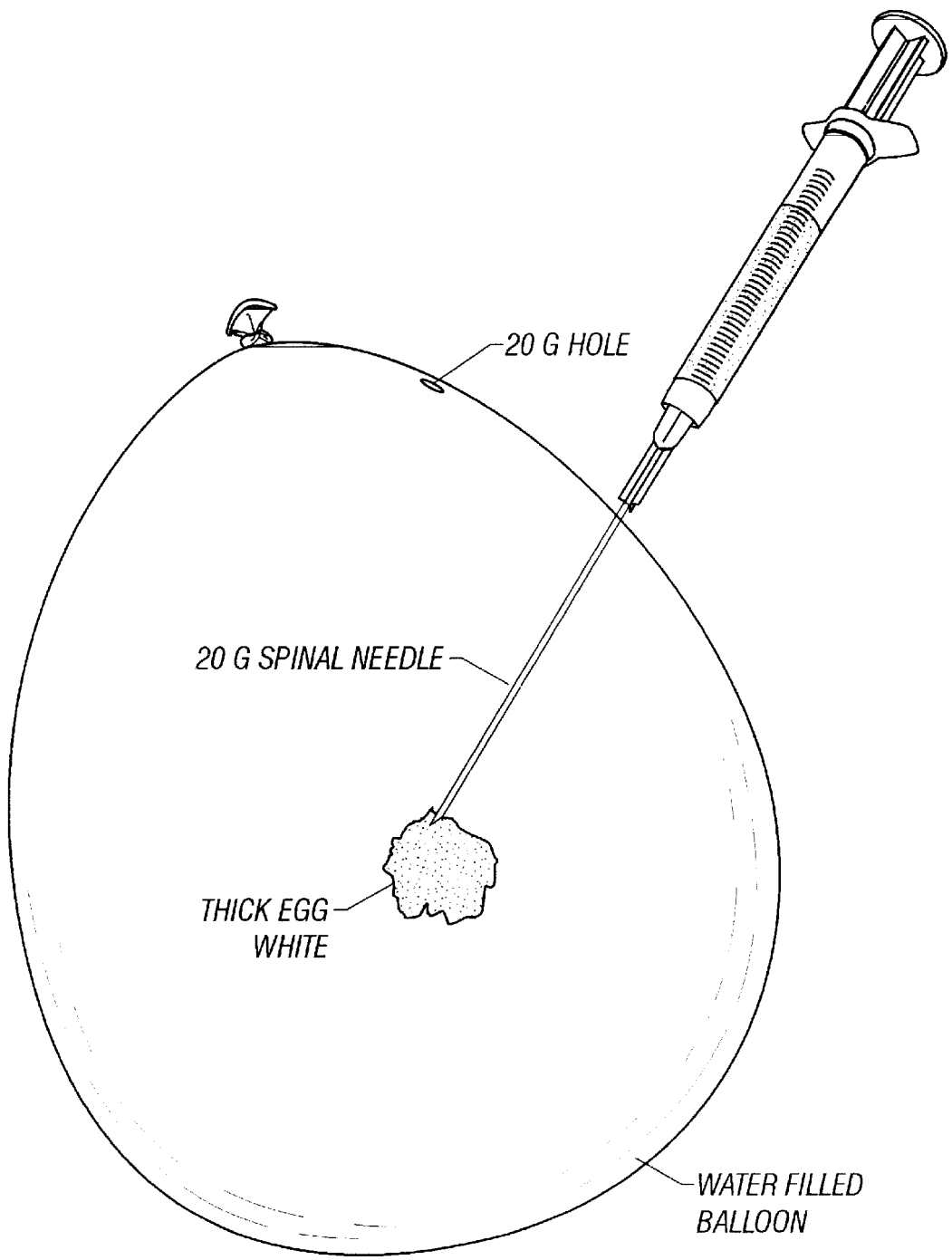
FIG. 1A Thick egg white injected into water filled balloon via 20G spinal needle.

Premature rupture of membranes (PROM) during pregnancy is currently attributed primarily to infection preceding rupture. More specifically, PROM is caused by rhexis of the amnion, especially in the area in contact with the uterine cervix. Rhexus of the amnion may be cause by (1) physical weakening of the amnion, (2) elevation of intrauterine pressure, and (3) dilation of the cervix. Infection may accompany each of these conditions, all of which interact with each other.

It has been discovered that amniotic fluid may not be sterile, contrary to previous beliefs. For example, Miller et al. (1980) showed that bacterial colonization of amniotic fluid might exist despite intact membranes, suggesting that bacteria can pass through the fetal membrane. Galask et al. (1984) demonstrated in vitro that anaerobes and group B streptococci (GBS) could easily invade the membrane.

Subclinical chorioamnionitis is believed to be a cause of idiopathic premature labor. Many genital bacteria are known to produce both phospholipase $A_2$ and phospholipase C, which can stimulate increased release of arachidonic acid and prostaglandin production within the uterus. Bejar et al. (1981) have shown that some genital bacteria release a phospholipase enzyme, thereby activating arachidonic acid metabolism in fetal membranes and stimulating the biochemical components of labor. Huddleston (1982) argues that the release of phospholipase $A_2$ from the fetal membrane triggers labor and leads to prostaglandin synthesis in the placental membrane.

Although the fetal membrane is normally very strong, clearly it is possible for it to become mechanically fragile. The only reasonable explanation for weakening of the membrane is colonization with vaginal flora. Bacterial invasion of the fetal membrane causes local inflammation, i.e., focal chorioamnionitis, with loss of membrane integrity leading to PROM. Bacterial enzymes and host products secreted in response to infection may add to the weakening and rupture of the membranes.

Resistance to infection depends on natural physiologic and mechanical barriers such as the endocervical mucus plug, intact fetal membranes and antimicrobial properties of amniotic fluid. PROM destroys those barriers. If PROM is left untreated, labor ensues, and the fetus is delivered with premature function of various organs. For example, when a baby is born with premature pulmonary function, he is likely to develop respiratory distress syndrome (RDS). Severe prematurity and immature epithelial lining of the germinal matrix in the brain or of the lining of the inter intestines can predispose the neonate to intraventricular hemorrhage (IVH) and necrotizing enterocoliter (NEC), respectively. Therefore, it is desirable to prolong the gestation of the fetus.

Typically, a patient who has suffered premature membrane rupture is immobilized in bed and sometimes given a tocolytic agent and an antibiotic. This treatment has often not proved sufficient to prevent maternal and fetal infections or labor, thus still often resulting in premature birth. Thus, while the infusion of antibiotics and other agents may be helpful, it would be more effective to provide some sort of physical plug or barrier to ascending infection. Such a barrier would also prevent the leakage of amniotic fluid out of the amniotic sac and aid in prolonging the gestation.

The inventor has discovered that the gelatinous nature of avian egg white and proteins within it are effective to create a seal of a membrane rupture when injected into the amniotic sac. While it is believed that the white from virtually any avian egg will be effective in the methods of the present invention, the examples herein focus primarily on the chicken egg white.

Chicken egg white is a cross species analog to amniotic fluid, providing protection, cushioning, and nutritive substances essential to the survival of the unborn chick. The cross linking of this colloid substance at the site of membrane rupture in the human gestation may provide an adequate sealant in the event of PROM. The inherent properties of egg white colloid include immiscibility with water (hydrophobic), thus creating a bolus effect when encountering the leakage site after injection into a water filled cavity. The most gelatinous portion of the thick egg white component is of substantially low enough viscosity to allow injection via a standard 18 to 20 gauge spinal needle commonly used for amniocentesis.

Chicken egg white exists as layers of thick egg white and thin egg white. The total egg white is more than 50% thick egg white, which is anchored by the chalazae to the surface of the yolk membrane. The chalazae and at least part of the thick egg white are closely related physically and probably chemically. In fact, the chalazae cannot be removed from the egg without tearing it from the egg white. The fibers of chalazae appear to become finer and finer until they admix and "disappear" into the thick egg white.

Thick and thin egg white differ both physically and chemically. Physical separation of the thick and thin egg white is currently only possible by crude and approximate means. The most simple and obvious method is to cut the thin and thick white away from one another in the brokenout egg. Another commonly used method is to separate the egg whites by means of passing the egg white through sieves with large diameter holes. Ovomucin has been purified to about 90% purity by French scientists using a Sepharose gel electrophoresis process.

The chemical differences between the thick and thin egg white include the following: When egg white is diluted and acidified, approximately four times the amount of precipitate is obtained from thick egg white as from thin egg white. This precipitate is called crude ovomucin. Ovomucin is believed to be the component responsible for the sealant properties of the egg white in the present invention. Additionally, thick egg white contains approximately four times the amount of inhibitory activity against the hemagglutination of erythrocytes by viruses. Thick egg white also contains approximately 30–40% more N-acetyl-neuraminic acid (sialic acid) than does thin egg white.

Chalazae, extracts of crude yolk membranes, and ovomucin also possess certain similarities between them. For example, all three are relatively high in sialic acid and in inhibitory activity for viral hemagglutination. These similarities support the hypothesis that the fibers in thick egg white, the chalazae, and the contiguous layer of thick egg white which is intimately associated with the true yolk membrane are closely related, if not identical, substances. These observations are also consistent with Conrad and Phillips' hypothesis that the chalazae is formed from the ovomucin fibers in the thick egg white as the egg passes down the hen's oviduct. Conrad and Phillips (1938) speculate that while the entire egg rotates slowly during its oviductal passage, the yolk remains steady and does not rotate with the rest of the egg. As a consequence, the ovomucin fibers are slowly turned and twisted into what eventually becomes the chalazae. There are, however, no direct observations to substantiate this attractive mechanical theory for the formation of chalazae.

The egg white is known to be primarily a solution of proteins with a relatively small amount of sugar and salts. Hence, the biochemist generally prefers to use avian egg white when he desires to separate, fractionate, and prepare purified proteins in quantity. That the egg white is primarily a solution of proteins makes the job of protein separation and purification much easier than with many other biological materials. Indeed, several egg white proteins have become standard proteins for biochemists. For example, chicken ovalbumin and lysozyme have been two of the less expensive and highest purity proteins available for many years.

The primary protein of chicken egg white is ovalbumin. The concentration of ovalbumin in egg white is about four to five times the concentration of the secondary constituents, ovotransferrin, and ovomucoid. Thus, ovalbumin provides the primary properties of egg white with the other constituents contributing mainly to the biological properties of the egg white. Ovumucin is an exception to this general rule. Ovomucin appears responsible for the high viscosity of thick egg white.

Many different procedures are available for fractionating chicken egg white for the preparation of the individual proteins. These procedures are well within the skill or the ordinary artisan and include salt fractionation techniques and fractionation with cellulose ion-exchange agents. Additionally, serial acidification, precipitation, centrifugation and alkali resuspension can be used to separate and purify ovomucin.

PROPERTIES OF EGG-WHITE PROTEINS

Ovalbumin is the principal protein of chicken egg white and is also the only major constituent for which no unique biochemical activity has been found. The main property of ovalbumin has been its sensitivity to denaturation. Ovalbumin is known to have some interesting chemical aspects not directly related to sequence. One such interesting aspect is its heterogeneity due to the presence of either one or two phosphates. Another interesting aspect is the number and reactivity of the cysteine sulfhydryl groups. Yet another is the structures of the side-chain carbohydrates and linkages of the carbohydrates to the peptide chain.

Avidin is another protein prominent in egg white. In 1941 Eakin, Snell, and Williams concentrated avidin using acetone and salt fractionation procedures. They then performed a modified biotin microbial assay designed for avidin. A unit was defined as the amount of concentrate capable of inactivating 1 gram of biotin. Raw egg white varied from 0.8 to 1.2 units/cc. Free avidin appears to be an albumin-like protein, although it probably occurred in egg white to varying extents as the above mentioned complexes.

Chicken egg-white flavoprotein (or ovoflavoprotein) is one of two egg-white proteins which contains, or can bind, a B-vitamin. The other is avidin. Rhodes, Bennett, and Feeney (1959) found ovoflavoprotein to exist in two forms; one form, flavoprotein, contains riboflavin and the other, apoprotein, does not. The total concentration of the two forms is approximately 0.8% of the egg white.

Ovomacroglobulin is the only detectable component of avian egg whites to have a wide spectrum of immunological cross-reactivity. It also appears to be strongly immunogenic. Deutsch (1953) reported that a large part of the capacity of egg white to produce antibodies was probably a minor unrecognized fraction of the egg white. The ovomacroglobulin might be this fraction.

Ovomacroglobulin is a very large protein with an estimated molecular weight of approximately 800,000 g/mole as determined by sedimentation-velocity, diffusion, and light scattering measurements. This makes ovomacroglobulin the largest recognized egg-white protein, other than ovomucin. There is, however, evidence that it dissociates into smaller units in acid solution.

In addition to the major proteins already described, there are probably one or two dozen minor proteins in chicken egg white. Several of these have been seen in different types of electrophoretic patterns of the egg white itself and probably many more have been seen as minor contaminating substances on purification of the recognized constituents. Lineweaver and co-workers (1948) found chicken egg white to be essentially devoid of enzymatic activities with the exception of catalase activity.

Some of the egg white proteins are known to have antimicrobial activity. It is believed that those proteins that do show antimicrobial or antienzyme properties could potentially be used as microbial antagonists. These include lysozyme, ovoflavoprotein, avidin, ovotransferrin, and the inhibitors of proteolytic enzymes, ovomucoid, and ovoinhibitor. For example, lysozyme has been shown to be bactericidal to a limited number of species. Ovotransferrin has also proven to be an important antimicrobial substance. Egg white typically has a high pH during the first few days of the incubation of the egg. This high pH egg white also has antibacterial activity, a factor that is usually overlooked.

The pH of the egg white in a freshly laid chicken egg is slightly below 7.6 and the pH of the yolk is approximately 6.0. The initial pH of 7.6 obviously closely approximates the pH of blood serum. Since the egg shell contains approximately ten thousand pores, carbon dioxide escapes through the shell and the pH of the egg white begins increasing immediately after the egg is laid. The rate of the pH increase depends on the temperature and the carbon dioxide tension. The pH will rise to above 8.0 within a matter of three or four hours at room temperatures. It appears that the egg white has such a high carbon dioxide content because a high carbon dioxide tension exists in the oviduct.

Physical changes in the egg contents occur after a few days at room temperature or a few weeks at refrigerated temperature. These changes include a weakening and dissolution of the gel of the thick egg white and a weakening and eventual rupturing of the yolk membrane. The rate at which these changes occur depends on the pH of the egg white and the temperature of incubation. The physical changes themselves are well known to anyone who has broken out a partially deteriorated egg and observed the watery white and perhaps rupturing of the yolk membrane. For this reason, it is believed that the egg white should be used within about 2 days if maintained at room temperature, preferably within about 24 hours. The composition could typically be usable for up to 2 weeks after purification and resuspension in a pharmaceutically acceptable carrier. Most preferably, the composition will be maintained at body temperature, that is, at about 37° C. and will be used within about 24 hours.

Most investigators agree that the deteriorative process in the thick egg white involves changes of the ovomucin. It has been shown that egg white can be thinned and the yolk membrane weakened by adding small amounts of reducing agents such as mercaptans or sulfite. (Hoover 1940; MacDonnell et al. 1955). Several treatments that denature or inactivate protein prevented the changes. It was further shown that other deteriorative changes in egg white were most evident by changes in the ovotransferrins. These changes were apparently due to interactions of the proteins with the glucose naturally present in the egg white. This glucose-protein reaction (Millard) seems to be accelerated by alkaline conditions and egg white is known to be relatively alkaline. Such a glucose-protein reaction should not occur at room temperature (or 37° C.) and in relatively dilute solution.

Several theories have been proposed for the deteriorative mechanisms in egg white. The first theory is that ovomucin is reductively cleaved by reducing agents generated during the incubation of the white. It is known that ovalbumin, which contains sulfhydryl groups, can be titrated with p-chloromercuricbenzoate. (MacDonnell et al. 1955). A "denaturation" of less than 1% of the ovalbumin is likely enough to supply the potential amount of reducing agent required to thin the egg white. Changes have been reported in the chromatographic characteristics, in the solubility, and in resistance to denaturation of ovalbumin.

The second theory is that lysozyme and ovomucin exist in a complex that both forms and dissociates during incubation. This changes the gel characteristics and causes thinning. The formation of a complex is supported by observations that the enzymatic activity of lysozyme in egg white decreases during incubation. In fact, the assayable activities of lysozyme in egg white were found to drop extensively (up to 40%) during the thinning process. The observed activity was dependent on the ionic strength during dilution of the egg white. These observations indicate an ionic type of complex involving lysozyme.

Another theory is that the solubility of ovalbumin changes during incubation. It has also been postulated that the interaction of glucose with protein directly or indirectly causes thinning. As discussed above, glucose interaction could indirectly cause thinning by generating reducing compounds.

Unfortunately, none of these theories fits all of the available data. Chicken, turkey (*Meleagris gallopavo*), and probably penguin (*Pygoscelis adeliae*) eggs deteriorate rapidly, while duck and goose eggs show essentially no deterioration. Duck eggs are relatively low in lysozyme and very low in sialic acid, which are both considered to be related to deterioration. The ovomucin fractions are known to contain sialic acid. Since the penguin egg contains essentially no lysozyme and the highest amount of sialic acid observed in any bird, these latter mechanisms seem improbable. Thus, a reduction mechanism or a combination of several mechanisms may be the cause of the changes finally expressed as a change in the colloidal distribution of the high molecular weight aggregates of ovomucin.

The inventor has found that a composition comprising avian thick egg white is effective to seal a membrane rupture. Since egg white is a benign composition, it is believed that injection of the purified thick egg white alone will be effective in the method of the invention. Alternatively, a composition containing ovomucin, the protein that causes the gelatinous nature of the egg white, may be used in the conjunction with the method of the invention.

In a preferred embodiment, the method of the invention includes administering a composition comprising substantially purified ovomucin in a pharmaceutically acceptable carrier in a therapeutically effective amount to a patient who has suffered a premature rupture of membrane. The term "substantially purified" refers to a ovomucin that has been isolated away from the other proteins present in thick egg white and purified to at least about 80% purity. It may also include synthetic ovomucin prepared to at least about 90% purity. Preferably, the isolate and purified ovomucin, either synthetic or natural, will be prepared to about 98% purity. It is also envisioned that active fractions or epitopes of the ovomucin protein may be effective in the present invention. Protein analysis to locate active epitopes and active portions of the protein chain, and preparation of peptide fractions, or truncated proteins, are well known and routine to those skilled in the art.

In preferred embodiments the composition may also contain one or more antibiotic or antimicrobial agents. For example, antimicrobials which will be effective in the present invention include injectable penicillins or their derivatives, injectable cephalosporins or their derivatives, injectable microlide antibiotics or their derivatives, injectable aminoglycoside antibiotics or their derivatives or other naturally occurring bacteriocidal and/or bacteriastatic substances found in egg white matrix. The antimicrobials will be present in the composition in a therapeutically effective amount, that is, in an amount effective to eliminate or inhibit bacteria present in the amniotic sac due to ascending infection or otherwise. The antimicrobials for inclusion in the compositions of the invention will generally be present in concentrations that provide bacteriocidal activity based on a minimum inhibitory concentration in the presence of a maximum dilution of about 3,000 mL of amniotic fluid.

The compositions of the invention will be injected directly into the ruptured amniotic sac of a patient who has suffered from premature rupture of membranes (PROM). Preferably, the compositions of the invention will be injected using an 18 gauge or a 20 gauge spinal needle, although it is envisioned that other sized needles, such as 18 to 25 gauge needles of variable length may be used in conjunction with the method of the invention. Preferably, about 5 to about 20 ccs will be injected into the patient's amniotic sac. Most preferably, about 10 ccs will be injected into the patient who has suffered from premature rupture of membrane.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all such cases, the form must be sterile and must be fluid to the extent that easy syringability exists. It must be stable under the conditions of manufacture and storage and must be preserved against the contaminating action of microorganisms, such as bacteria and fungi.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thiomerisal, and the like. In many cases, it will be preferable to include isotonic agents, for example, sugars or sodium chloride. Prolonged absorption of the injectable compositions can be brought about by the use in the composition of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously-sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

EXAMPLE 1

Figure 1B:
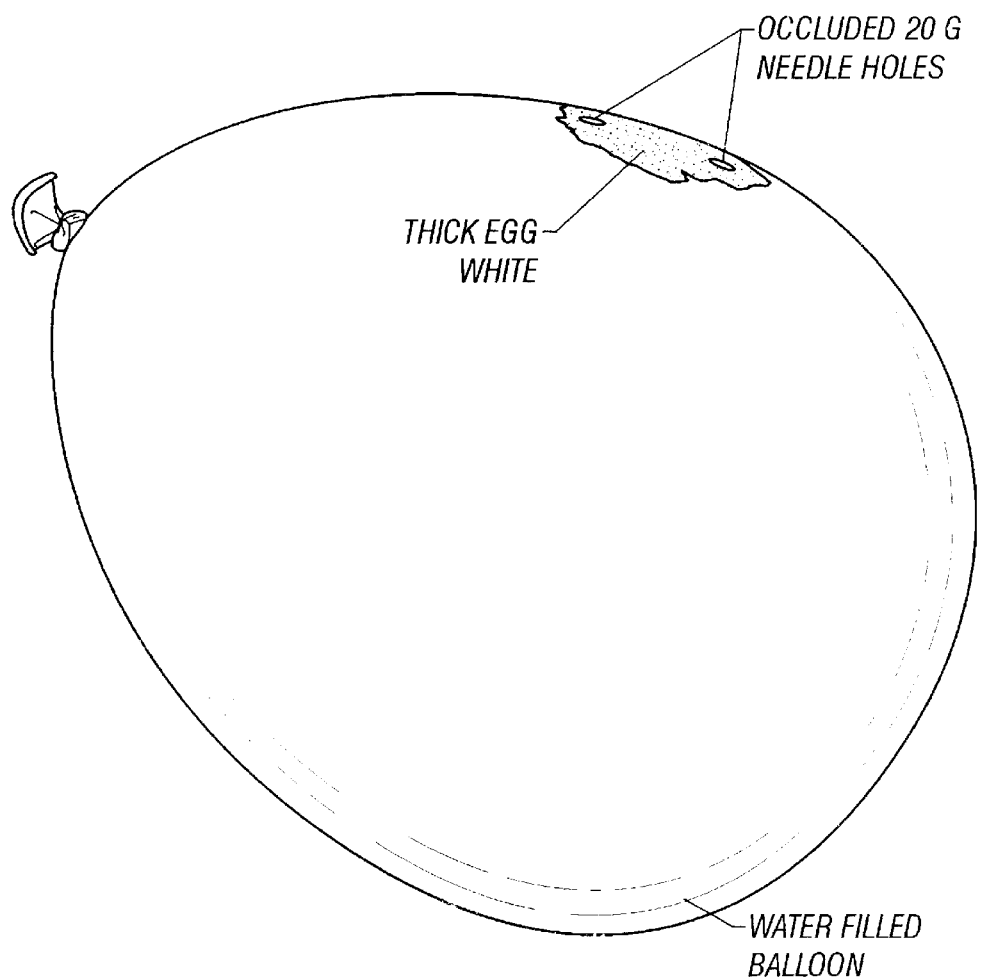
FIG. 1B Successful occlusion of 20G holes in balloon by thick egg white.

Nine inch diameter helium grade water filled balloons were initially used as an in vitro model of the amniotic membrane. The internal pressure as measured by manometry was between 25–35 cm of water. Hypodermic needles of standard medical grade were used to create puncture holes in the water filled balloons. Initially, single 20 gauge (1.0 mm) holes were created through which 5 mL of thick egg white were injected into the water filled balloons (See FIG. 1A). The hydrophobic egg white remained immiscible with water. When the egg white bolus contacted the inner surface at the leak site, the hole was successfully plugged (FIG. 1B). These seals were maintained for three weeks, at which time, the integrity of the rubber of the balloon itself began to degrade. Of note, the seal appeared more readily when the water inside the balloon was approximately equal to body temperature (37° C.) as regulated by a digital thermometer.

EXAMPLE 2

Repeated acetic acid elutions were performed on thick egg white. Repeated elutions with 5% acetic acid followed by washing with water led to thickened and precipitated membrane in the thick egg white. The thin egg white was easily separated from the thick egg white in the soluble form. Resuspension occurred when the pH was made basic using ammonia. Precipitation again occurred when acidic conditions were reinstated. Thus, it appears that the components of thick egg white are stable to changes in pH of the suspending solution, but the viscosity is markedly increased in acidic environments.

EXAMPLE 3

Figure 2:
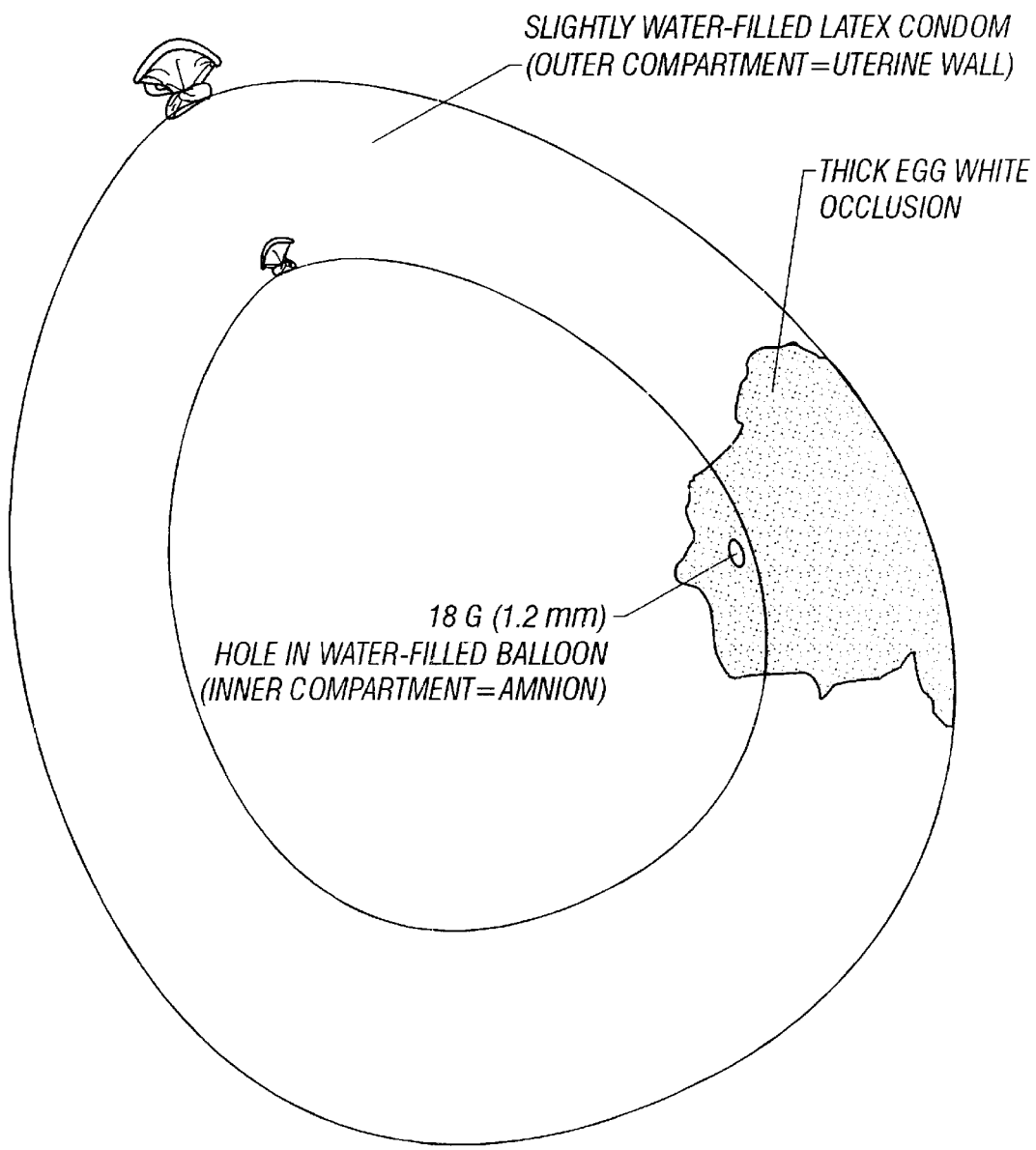
FIG. 2 Condom-balloon apparatus simulating uterine lining (condom) and amnion (balloon). Successful occlusion using thick egg white.

A dilute (5%) acetic acid was used to thicken and precipitate the thick egg white. The more viscous component was separated from the remaining egg white components. A nine-inch helium-grade balloon was then filled with water and 4 mL of acid eluted thick egg white. The balloon (inner membrane) was then placed inside a slightly water filled latex condom. This apparatus simulates the inner membrane (amnion) and outer compartment (uterus). A single 18 gauge (1.2 mm) hole was created by passing a hypodermic needle through the balloon. The thick egg white within the balloon migrated to the leak site and readily sealed the leak at the balloon/condom interface (FIG. 2). The seal was readily visualized through the transparent condom.

EXAMPLE 4

Figure 3:
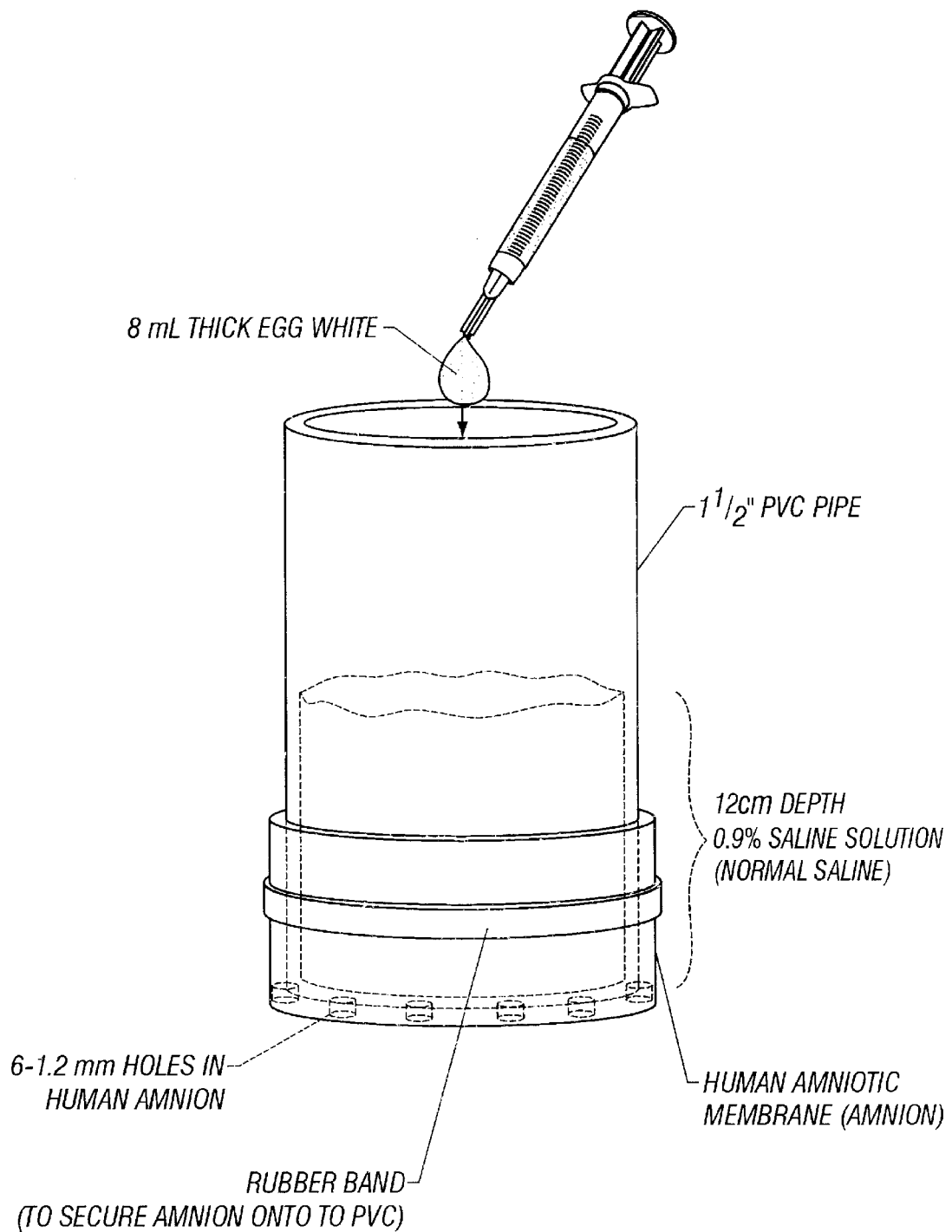
FIG. 3 Physiologic in vitro evaluation of thick egg white occluding six 1.2 mm (18G) holes in human amnion. Saline solution was utilized to recreate a resting uterine tone of 12 cm water pressure.

Amniotic membranes from human placentas were utilized to more accurately assess in vivo activity of the thick egg white physical characteristics. Membranes from normal term placentas were attached to the distal end of a 12-inch long 1 ½ inch diameter common polyvinyl chloride (PVC) pipe. A single rubber band was used to secure a 12 cm×12 cm square of amnion to the PVC pipe. Normal saline solution (0.9%) was used to fill the proximal end of the pipe to the gravitational equivalent pressure to the resting tone of a pregnant uterus. Approximately 8 mL of thick egg white was introduced into the proximal end of the pipe. Six 18-gauge (1.2 mm) holes were punctured through the amniotic membrane (FIG. 3). All holes were readily sealed using the above apparatus.

The same apparatus was utilized while creating a single 1 cm tear in the amnion. The saline and egg white solution failed to seal this size tear. It is believed that the leakage through such a tear in an actual human amniotic membrane would be lessened in vivo in a system with endometrium and outer compartment (uterus) containing the inner membrane due to increased surface area and surface tension. The flow across the in vivo system would be markedly less than the full gravitational forces present in this example.

The above procedure was repeated using holes of sizes 25 gauge, 22 gauge, 20 gauge and 18 gauge and a range of pressures of 10 cm, 20 cm and 30 cm of water. Some suggestion of slow leak was observed with 30 cm of water only with the 18 gauge hole. Identical results were observed using both thick meconium and normal amniotic membrane specimens suspended on PVC pipe.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Awade, A. C. et al., Two-step chromatographic procedure for the purification of hen egg white ovomucin, lysozyme, ovotransferrin and ovalbumin and characterization of purified proteins, J. CHROMAT. A, 677: 279–288 (1994).

Awade, A. C. and Efstathiou T., Comparison of three liquid chromatographic methods for egg-white protein analysis, J. CHROMAT. B, 723: 69–74 (1999).

Bejar, R. et al., Premature labor. II. Bacterial sources of phospholipase, OBSTET. GYNECOL. 57: 479 (1981).

Conrad, R. M. and Phillips, R. E., The formation of the chalazae and inner thin white in the hen's egg, POULTRY SCI.17: 143 (1938).

Deutsch, H. F., Immunochemical analysis of egg white, FED. PROC., 12: 729 (1953).

Eakin, R. E. et al., The concentration and assay of avidin, the injury-producing protein in raw egg white, J. BIOL. CHEM. 140:535 (1941).

Feeney, R. E. and Allison, R. G., In *Evolutionary Biochemistry of Proteins: Homologous and Analogous Proteins from Avian Egg Whites, Blood Sera, Milk, and Other Substances*, Wiley-Interscience (1969).

Galask, R. P. et al., Bacterial attachment to the chorioamniotic membranes, AM. J. OBSTET. GYNECOL. 148: 915 (1984).

HANDBOOK OF BIOCHEM. AND MOLECULAR BIO., 3D EDITION, Volume II, Gerald D. Fasman (Editor), CRC Press pp. 268–269, 486, 533, 721 (1976).

Hoover, S. R., *A physical and chemical study of ovomucin*, Ph. D. Thesis, Georgetown Univ., Washington, D.C., (1940).

Huddleston, J. F., Preterm labor, CLIN. OBSTET. GYNECOL. 25: 123 (1982).

Imanaka & Ogita, New Technologies for the Management of PPROM, OBSTETRICS & GYNECOLOGY CLINICS OF N. AM., 19(2): 366–386 (1992).

Kirkovsky, V. V. et al., Biospecific haemosorbents based on proteinase inhibitor; III. Biospecific antiproteinase haemosorbent "Ovosorb" in complex therapy of acute destructive pancreatitis, BIOMATERIALS, 15(5): 334–336 (1994).

Kishaw, P. J. and Cant, A. J., The Passage of Maternal Dietary Proteins into Human Breast Milk, INT. ARCHS ALLERGY APPL. IMMUN. 75: 8–15 (1984).

Lineweaver, H. et al., Enzymes of fresh hen eggs, ARCH. BIOCHEM. 16: 443 (1948).

MacDonnell, L. R. et al., The functional properties of the egg-white proteins, FOOD TECHNOL. 9:49 (1955).

Miller, J. M. et al., Bacterial colonization of amniotic fluid from intact fetal membranes, AM. J. OBSTET. GYNECOL. 136:796 (1980).

Platé, N. A. et al., Biospecific haemosorbents based on proteinase inhibitor: I. Synthesis and properties, BIOMATERIALS 14(1): 51–56 (1993).

Platé, N. A. et al., Biospecific haemosorbents based on proteinase inhibitor: II. Efficiency of biospecific antiproteinase haemosorbent 'Ovosorb' in complex treatment of experimental generalized purulent peritonitis and acute destructive pancreatitis in dogs, BIOMATERIALS 15(4): 285–288 (1993).

Rabouille, C. et al., Interactions Involved in Ovomucin Gel-Forming Properties: A Rheological-Biochemical Approach", ARCHIVES OF BIOCHEM. & BIOPHYS., 270(2): 495–506 (1989).

Rabouille et al., The Supramolecular Organization of Ovomucin. Biophysical and Morphological Studies, BIOCHEMICAL JOURNAL, 266(3): 697–706 (1990).

Rhodes, M. B. et al., The flavoprotein-apoprotein system of egg white, J. BIOL. CHEM. 234: 2054 (1959).

Stevens, L., Egg White Proteins, COMP. BIOCHEM. PHYSIOL. 100B(1): 1–9 (1991).

Strecker, G. et al., $^1$H and $^{13}$C-NMR assignments for sialylated oigosaccharide-alditols related to mucins. Study of thirteen components from hen ovomucin and swallow nest mucin, BIOCHIMIE 74: 39–52 (1992).

What is claimed is:

1. A method of sealing a ruptured amniotic membrane comprising introduction of an effective amount of an avian thick egg white composition into an amniotic fluid sac of a mammal.

2. The method of claim 1, wherein said avian egg white composition is a chicken thick egg white composition.

3. The method of claim 1, wherein said thick egg white composition further comprises a pharmaceutically acceptable carrier.

4. The method of claim 1, wherein said thick egg white composition comprises an ovomucin composition.

5. The method of claim 4, wherein said ovomucin composition comprises ovomucin in the range of 1 to 90 percent by weight.

6. The method of claim 1, wherein said thick egg white composition is introduced into said amniotic sac by an injection procedure.

7. The method of claim 6, wherein said injection procedure is an amnioinfusion procedure.

8. The method of claim 1, wherein said thick egg white composition further comprises one or more antibiotics, or bacterial inhibiting substances.

9. A method of enhancing the integrity of a ruptured amniotic membrane comprising contacting said ruptured amniotic membrane with an effective amount of an avian egg white glycoprotein composition.

10. The method of claim 1, wherein said avian egg white composition is a chicken thick egg white composition.

11. The method of claim 1, wherein said thick egg white composition further comprises a pharmaceutically acceptable carrier.

12. The method of claim 1, wherein said thick egg white composition comprises an ovomucin composition.

13. The method of claim 12, wherein said ovomucin composition comprises ovomucin in the range of 1 to 90 percent by weight.

14. The method of claim 1, wherein said thick egg white composition is introduced into said amniotic sac by an injection procedure.

15. The method of claim 14, wherein said injection procedure is an amnioinfusion procedure.

16. The method of claim 1, wherein said thick egg white composition further comprises one or more antibiotics, or bacterial inhibiting substances.

17. A pharmaceutical amniotic membrane sealant composition comprising an effective amount of a sterile avian egg white glycoprotein composition and one or more pharmaceutically acceptable preservatives.

18. The composition of claim 17, further comprising a pharmaceutically acceptable carrier.

19. The composition of claim 18, further comprising an antimicrobial agent in a therapeutically effective amount.

20. A kit for use in a method of sealing a ruptured amniotic membrane, said kit comprising a thick egg white glycoprotein composition in a suitable vial or container.

21. The kit of claim 20, wherein the thick egg white composition comprises isolated and purified ovomucin with a purity of about 80% to about 95%.

22. The kit of claim 21, wherein the egg white composition may be in powder form or gel form or in a solution comprising a pharmaceutically acceptable preservative with or without a pharmaceutically acceptable carrier.

* * * * *